United States Patent [19]
Leal

[11] Patent Number: 5,199,872
[45] Date of Patent: Apr. 6, 1993

[54] DENTAL APPLIANCE

[76] Inventor: Francisco G. B. Leal, Rua Vicente Leite 1011 Apt. 200, Fortaleza/Ce, Brazil, 60.170

[21] Appl. No.: 804,450

[22] Filed: Dec. 10, 1991

[51] Int. Cl.⁵ ............................. A61C 5/14; A61C 5/00
[52] U.S. Cl. ...................................... 433/136; 433/140
[58] Field of Search ......................... 433/136, 138, 140

[56] References Cited

U.S. PATENT DOCUMENTS

| | | |
|---|---|---|
| 151,265 | 5/1874 | Bancroft . |
| 692,281 | 2/1902 | Hare . |
| 927,850 | 7/1909 | Gartrell . |
| 1,010,147 | 11/1911 | Ivory . |
| 2,614,325 | 10/1952 | Hartig ................................. 433/138 |
| 2,623,284 | 12/1952 | Ackley . |
| 2,651,109 | 9/1953 | Kanter ................................ 433/140 |
| 2,885,783 | 5/1959 | Golden . |
| 3,396,468 | 8/1968 | Dayhoff .............................. 433/140 |
| 4,053,984 | 10/1977 | Moss .................................. 433/140 |
| 4,071,955 | 2/1978 | Julius ................................. 433/136 |
| 4,259,067 | 3/1981 | Nelson ................................ 433/93 |
| 4,600,387 | 7/1986 | Ross ................................... 433/136 |
| 4,820,155 | 4/1989 | Sauveur .............................. 433/136 |

FOREIGN PATENT DOCUMENTS 2741899 3/1979 Fed. Rep. of Germany .
1249006 10/1971 United Kingdom ................ 433/140

Primary Examiner—John J. Wilson
Assistant Examiner—Cindy A. Cherichetti
Attorney, Agent, or Firm—Nixon & Vanderhye

[57] ABSTRACT

The dental appliance includes a generally elliptical-shaped wire folded about a minor axis to form upper and lower, generally U-shaped sections having front and rearwardly extending leg portions. The leg portions are connected one to the other to enable resilient displacement of the upper and lower sections toward one another. In one form, a clamping element is pivotally secured to each of the upper and lower sections for securing a cotton roll between the element and sections whereby the cotton roll completely envelops the portions of the appliance which would otherwise bear against the soft tissue of the patient's mouth. In a further form, mesh is applied about the wire in lieu of the clamping element to secure a wrapping of flexible material about the wires forming the appliance, also protecting the soft tissues of the patient's mouth from the appliance.

14 Claims, 2 Drawing Sheets

DENTAL APPLIANCE

BACKGROUND AND SUMMARY OF THE INVENTION

The present invention relates to a dental appliance and particularly to a dental appliance for isolating the operative area of a patient's mouth and maintaining the patient's mouth in a open position, exposing such area. The present invention also relates to a reusable dental appliance, hence, an appliance capable of sterilization.

Many different dental appliances have been proposed and used in the past in efforts to maintain the patient's mouth in an open position and expose the operative area. Such appliances are often uncomfortable for the patient, both during insertion and retraction, as well as during the performance of the dental work. More particularly, many such appliances do not provide for the protection of the soft tissues of the mouth and often bear against such tissues during insertion, withdrawal and use, even to the extent of causing injury. Additionally, certain appliances of this type do not provide for the removal of saliva from the patient's mouth and rely on apparatus ancillary to the appliance for such removal. Other appliances of this type afford saliva removal both require a substantially enlarged appliance to accommodate the saliva removal. The larger size limits access to the operative area. Still further, certain prior art appliances of this type cannot be sterilized and, hence, are not reusable.

According to the present invention, there is provided a dental appliance which minimizes or eliminates many of the foregoing and other disadvantages of the prior art appliances and provides a novel and improved dental appliance, the principal features of which provide for isolation of the operative area of the patient's mouth and prevents the patient from closing his mouth during the performance of the dental work. Additional features of the present invention include an appliance having an all-metal construction whereby it may be sterilized and, hence, reused, an adaptability for use with conventional cotton rolls widely used in dental practice for absorbing saliva and isolating the operative area, a specific construction which facilitates insertion and withdrawal of the appliance to and from the patient's mouth, respectively, and a tongue depressor forming part of the appliance whereby the patient's mouth is not only maintained in an open condition but the tongue is depressed from the operative area.

To accomplish the foregoing and other objects of the present invention, there is provided a dental appliance comprised of upper and lower generally U-shaped sections, preferably formed of a metallic wire with each section having a front portion and transversely spaced leg portions. The upper and lower leg portions are secured one to the other along opposite sides of the appliance and adjacent the rear portion thereof in a manner permitting the upper and lower sections to be resiliently displaced from a predetermined orientation toward one another and back to such orientation. The displacement of the sections toward one another facilitates insertion and withdrawal of the appliance relative to the patient's mouth and the resiliency of the appliance imparts a bias to maintain the appliance in the predetermined orientation and hence when inserted, maintain the patient's mouth in an open position.

In the embodiment hereof wherein the appliance is formed of metallic wire, the appliance may be formed by providing a metallic wire in a closed elliptical form and bending the wire about its minor axis to provide semi-elliptical sections spaced one from the other, and open at the front of the appliance to facilitate access between those sections and to the operative area when placed in the patient's mouth. Preferably, a tab projects from the front portion of each of the upper and lower sections to facilitate displacing the upper and lower sections toward one another for insertion and removal of the appliance relative to the patient's mouth. Also, a generally U-shaped wire is secured to opposite transversely spaced rear portions of the appliance and extends forwardly generally in the plane of the lower section to form a tongue depressor. The ends of the wire forming the depressor are secured to the upper and lower sections adjacent the pivotal axis of the sections. The flexible material may also have absorbent properties for absorbing saliva.

In one form of the present invention, a pair of elements, generally semi-elliptical in shape, are pivotally secured to the rear end portions of the upper and lower sections and extend between and are spaced from the sections to form upper and lower clamps. These clamps releasably secure a flexible cushioning and absorbent material along the upper and lower sections. More particularly, cotton rolls may be applied to one or the other of the upper section or associated clamping element by slitting the rolls lengthwise and inserting the section or element lengthwise along the slit. The element thus clamps a portion of the cotton roll between the element and upper section to maintain the roll in position, not only to cushion the appliance within the patient's mouth but also to absorb saliva. The cotton rolls may similarly be applied along the lower section and its associated clamping element, along the leg portions of the upper and lower sections, and along the tongue depressor. The cotton rolls are movable with the upper and lower sections during insertion and withdrawal of the appliance.

In another embodiment of the present invention and to provide for the patient's comfort when the appliance is disposed in the patient's mouth, the upper and lower sections may be wrapped with a flexible cushioning material. In this form, the material bears and cushions between the gums and the lips when inserted. The cushioning material is retained on the upper and lower sections by a wire mesh material secured to those sections. By wrapping the flexible material about the mesh, the mesh grasps the material, and secures it in place about the sections. The flexible material may also have absorbent properties for absorbing saliva.

After use and with respect to either embodiment, the appliance is removed from the patient's mouth and the flexible/absorbent material is removed from the appliance, leaving an all-metal structure, which can be sterilized for reuse.

In a preferred embodiment according to the present invention, there is provided a dental appliance for isolating an operating area of the mouth of a human patient and maintaining the mouth in an open position comprising a frame including upper and lower generally U-shaped sections in spaced relation one to the other and generally conformal in shape to the spaces between the upper gum and lip and lower gum and lip, respectively, of the mouth of a human patient, each section having a front portion and a pair of transversely spaced leg portions extending rearwardly from the front portion. The leg portions of said sections are connected to one another adjacent rear end portions thereof and transverse opposite sides of the appliance, the connected rear end leg portions form a resilient connection between the upper and lower sections, enabling movement of the upper and lower sections toward and away from one another about an axis extending generally transversely of the appliance. The resilient connection maintains the upper and lower sections spaced in an operative orientation a predetermined distance one from the other such that, upon placement of the appliance in a patient's mouth, the appliance maintains the patient's mouth in an open position. Means are carried by the frame for securing a flexible material along the front portions of each of the upper and lower sections thereof enabling the material to cushion the appliance frame between the gums and lips of the patient.

Accordingly, it is a primary object of the present invention to provide a novel and improved dental appliance for exposing operating areas within the patient's mouth, preventing the closing of the patient's mouth and affording improved comfort and saliva removal.

These and further objects and advantages of the present invention will become more apparent upon reference to the following specification, appended claims and drawings.

BRIEF DESCRIPTION OF THE DRAWING FIGURES

DETAILED DESCRIPTION OF THE DRAWING FIGURES

Reference will now be made in detail to a present preferred embodiment of the invention, an example of which is illustrated in the accompanying drawings.

Figure 1:
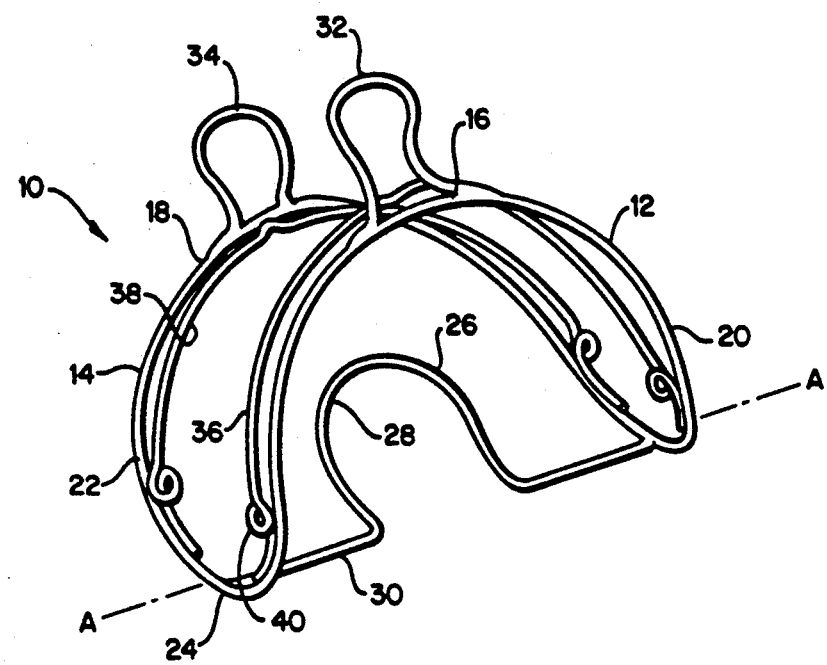
FIG. 1 is a perspective view of a dental appliance constructed in accordance with the present invention, illustrating its all-metallic wire construction.

Referring now to the drawings, particularly to FIG. 1, there is illustrated a preferred form of a dental appliance constructed in accordance with the present invention and generally designated 10. Appliance 10 comprises generally U-shaped upper and lower sections 12 and 14, respectively, with each section having a front portion 16 and 18, respectively, and transversely spaced rearwardly extending leg portions 20 and 22. Thus, the upper and lower sections 12 and 14, respectively, are generally semi-elliptical in shape. The leg portions 20 and 22 at transversely opposite sides of the appliance 10 are connected one to the other (in this form, integrally connected one to the other) at 24 in a manner such that the upper and lower sections 12 and 14 may be resiliently displaced toward and away from one another. The axis of this displacement lies generally along a line designated A—A in FIG. 1.

In the preferred form, appliance 10 is formed of a metallic wire. For ease of constructing the appliance 10, the wire forming the upper and lower sections 12 and 14 and the connective portions 24 may initially be formed into a flat elliptical shape. The opposite ends of the elliptically-shaped wire may then be folded or bent about the minor axis of the ellipse, i.e., about axis A—A, to space the two semi-elliptical portions forming the upper and lower sections 12 and 14, respectively, in the manner illustrated in FIG. 1. Consequently, the appliance 10 is open along its front side between front portions 16 and 18 and leg portions 20 and 22 of upper and lower sections 12 and 14, respectively, enabling access, when the appliance is disposed in a patient's mouth, to the operative area, as discussed hereinafter.

Also included as part of appliance 10 is a tongue depressor 26. Preferably, tongue depressor 26 also comprises a metallic wire which is secured, for example, by soldering to the rear end of the appliance adjacent the connective portions 24. The wire includes a base portion 30 which extends inwardly from the opposite sides of the appliance and then forms a generally U-shaped configuration 28, generally in the arcuate plane of lower section 14. Thus, the U-shaped tongue depressor 28 extends forwardly from the transversely extending base portion 30 of depressor 26.

Secured to the front portions 16 and 18 of upper and lower sections 12 and 14, respectively, are a pair of forwardly projecting tabs 32 and 34. These tabs may comprise wires which are secured to the wires forming the front portions 16 and 18 of the appliance. The tabs 32 and 34 are U-shaped in configuration and generally bowed to accommodate the dentist's fingers, so that the tabs may be used to displace the upper and lower sections 12 and 14, respectively, toward and away from one another to facilitate insertion and removal of the appliance relative to the patient's mouth.

Figure 2:
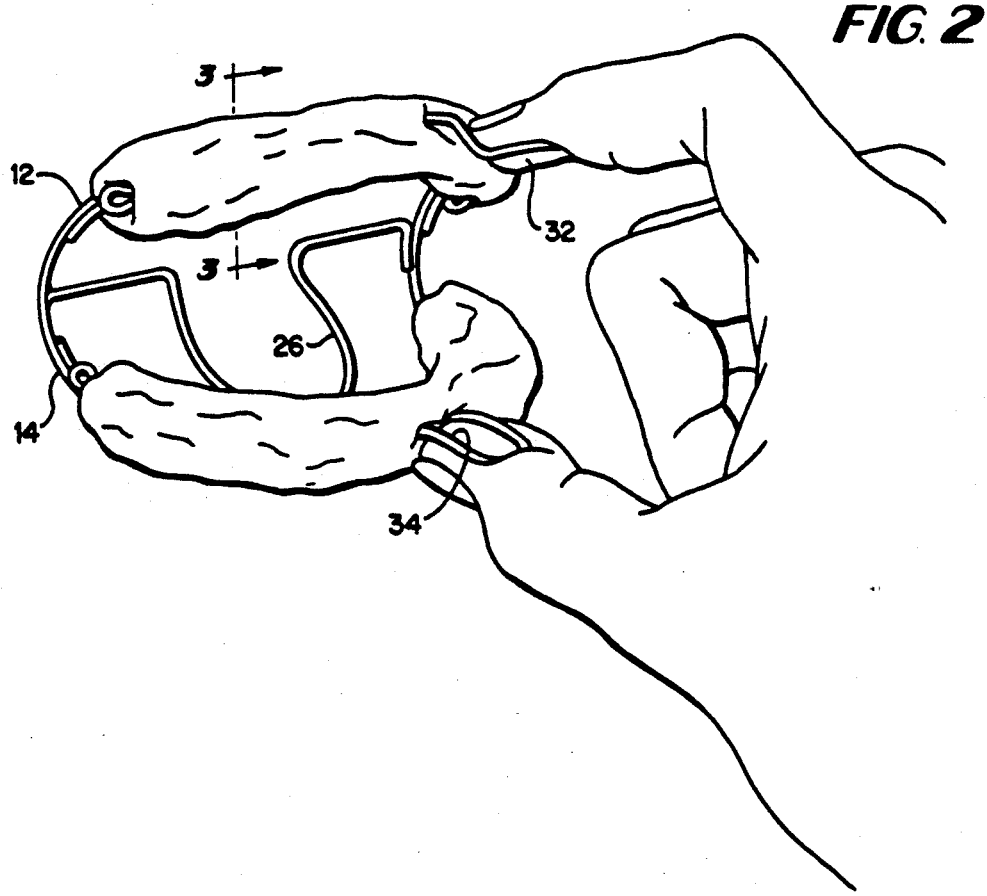
FIG. 2 is a perspective view of the appliance with flexible or absorbent material applied to its upper and lower sections and illustrating the manner of application of the appliance to the patient's mouth.
Figure 3:
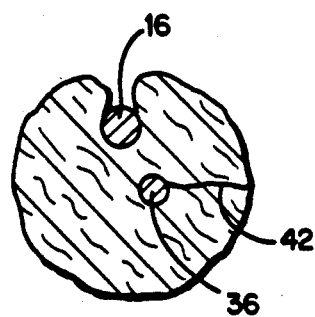
FIG. 3 is an enlarged cross-sectional view thereof taken generally about on line 3—3 in FIG. 2.

In this preferred form of the invention illustrated in FIGS. 1-3, there is additionally secured to the upper and lower sections 16 and 18 clamping elements 36 and 38, respectively. Clamping elements 36 and 38 each comprise wires which are shaped generally in conformance with the upper and lower sections 12 and 14 and which have one or more coils 40 adjacent their rear end portions whereby the elements 36 and 38 may be pivoted from their orientation spaced from the upper and lower sections to a position enlarging the space between the element and its corresponding section. Coil springs 40 thus bias elements 36 and 38 into the illustrated position spaced from the corresponding sections. The ends of elements 36 and 38 are secured to the wires forming rear portions of the upper and lower sections.

In a preferred form of the present invention, as illustrated in FIGS. 2 and 3, conventional cotton rolls may be applied to appliance 10 for purposes of cushioning the appliance with respect to the soft tissues of the patient's mouth and to provide for absorption of saliva. To releasably secure the cotton rolls to appliance 10, the cotton rolls are preferably slit lengthwise, as illustrated in FIG. 3, to form a transversely extending slit 42. The cotton roll may then be applied to the appliance by fixing it to one of the elements or wire portions of the upper and lower sections. Thus, for example, element 36 may be received through slit 42 whereby the cotton roll completely envelops element 36 for the lengthwise extent of the roll. Element 36 may be displaced away from the upper section so that a portion of the cotton roll may be disposed between the upper section and the element, also as illustrated in FIG. 3. Consequently, the wire portions of the upper section and element 36 lie within the peripheral confines of the cotton roll and hence do not bear against the soft tissues within the patient's mouth. By locating the cotton rolls along the front and leg portions of each of the upper and lower sections, as described, the soft tissues of the mouth are fully protected from the wire of the appliance, while simultaneously the cotton rolls absorb the saliva. The cotton rolls may also be applied in similar manner about tongue depressor 26 and about virtually any other portion of the appliance where it is deemed necessary to protect the soft tissue of the patient's mouth from the appliance.

With the cotton rolls applied as stated previously, appliance 10 may be inserted into the mouth of the patient. To accomplish this, the dentist grasps tabs 32 and 34 between his fingers and displaces the upper and lower sections toward one another. With the upper and lower sections displaced, the appliance is inserted into the patient's mouth. Once inserted, the pressure on the tabs 32 and 34 may be slowly released to locate the upper and lower sections, respectively, between the patient's upper gum and lips on the one hand and the lower gum and lip on the other hand. Tongue depressor 26, of course, is located to overlie the tongue to maintain the tongue in a depressed condition within the mouth. It will be appreciated that by releasing the tabs 32 and 34, the wire exerts pressure on the upper and lower jaws of the patient to maintain the mouth in an open position, while simultaneously isolating the area for dental work. Note also that the entire appliance is open along its front edge, facilitating access to the operative area by the dentist.

Figure 4:
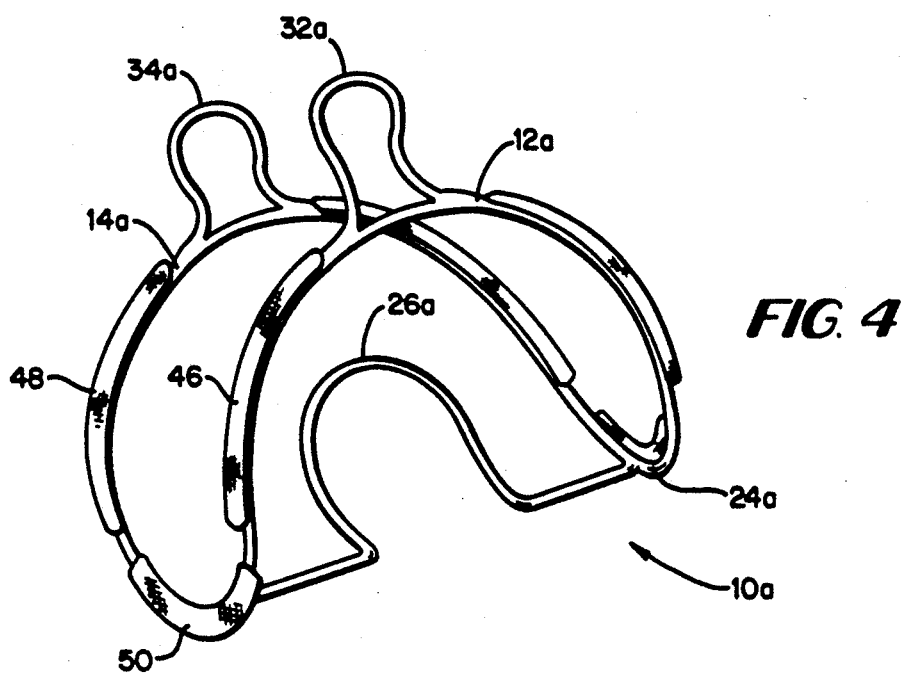
FIG. 4 is a view similar to FIG. 1 illustrating a further embodiment of the present invention.
Figure 5:
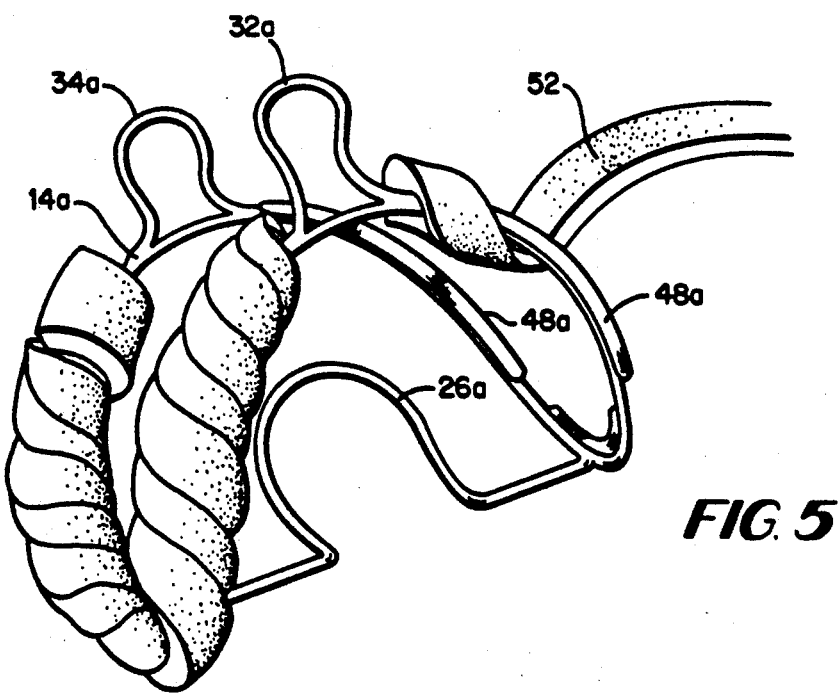
FIG. 5 is a view of the embodiment hereof illustrated in FIG. 4 illustrating the wrapping of flexible material about the upper and lower sections of the appliance.

Referring now to the embodiment hereof illustrated in FIGS. 4 and 5, like numerals are applied to like parts as previously described with respect to the embodiment hereof in FIGS. 1-3 and are followed by the suffix a. In this form, appliance 10a includes upper and lower sections 12a and 14a, preferably formed of wire, a tongue depressor 26a and tabs 32a and 34a. In this form, the elements 36 and 38 are omitted and additional wire mesh materials 46 and 48 are provided along the outside surfaces of the upper and lower sections 12a and 14a, respectively. Wire mesh material 50 may also be applied about the connective portion 24a of the wires forming the upper and lower sections 12a and 14a, respectively. The wire mesh 46, 48 and 50 may be suitably secured to the wires forming the appliance. The mesh material is employed in this form to secure a wrapping of flexible material 52 about the front and leg portions of the upper and lower sections, as well as about the connective portions of the appliance. The wrapping may be of any soft, flexible material and which material may also be absorbent.

As illustrated in FIG. 5, the portions of the appliance mounting the mesh material are wrapped with the material 52 whereby substantially the entirety of the wires and mesh material forming the appliance of this embodiment are covered by the flexible material. The appliance of this embodiment is used similarly as described with respect to the previous embodiment.

In both embodiments, it will be appreciated that the cotton rolls or flexible material may be removed from the appliance after use and discarded. In this manner, only the wire material of the appliance remains and this wire material can be placed in a sterilizer so that the appliance may be sterilized and reused.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A dental appliance for isolating an operating area of the mouth of a human patient and maintaining the mouth in an open position comprising:
   a frame including upper and lower generally U-shaped sections in spaced relation one to the other and generally conformal in shape to the spaces between the upper gum and lip and lower gum and lip, respectively, of the mouth of a human patient, each section having a front portion and a pair of transversely spaced leg portions extending rearwardly from the front portion and along opposite sides of the patient's mouth;
   the leg portions of said sections being connected to one another adjacent rear end portions thereof and transverse opposite sides of the appliance;
   said connected rear and leg portions forming a resilient connection between said upper and lower sections, enabling movement of said upper and lower sections toward and away from one another about an axis extending generally transversely of said appliance;
   said resilient connection maintaining said upper and lower sections spaced in a operative orientation a predetermined distance one from the other such that, upon placement of the appliance in a patient's mouth, the appliance maintains the patient's mouth in an open position;
   said upper U-shaped section including the front portion and the pair of transversely spaced leg portions of said upper U-shaped section lying in a first plane, said lower U-shaped section including the front portion and the pair of transversely spaced leg portions of said lower U-shaped section lying in a second plane, said first and second planes in said operative orientation of said appliance intersecting one another along a line generally parallel to the axis and rearwardly of the axis; and
   means carried by said frame for securing a flexible, absorbent material along the front portions of each of the upper and lower sections thereof enabling the material to cushion the appliance frame between the gums and lips of the patient.

2. An appliance according to claim 1 wherein said securing means includes a pair of elements connected to said frame and extending along and in spaced, generally parallel relation to said upper and lower sections for securing at least part of the flexible material between said elements and said upper and lower sections, respectively.

3. An appliance according to claim 2 wherein said elements are secured to said frame for resilient movement toward and away from the respective upper and lower sections.

4. An appliance according to claim 1 in combination with the flexible material, wherein said securing means includes a pair of elements connected to said frame and extending along and in spaced, parallel relation to said upper and lower sections, respectively, for securing at least part of the flexible material between said elements and said upper and lower sections, respectively.

5. The combination according to claim 4 wherein said flexible material includes a pair of cotton rolls split lengthwise to form slits, said rolls being disposed on said upper and lower sections, respectively, with one of said front portion and said element being received within the longitudinal slit of said cotton roll in each upper and lower section.

6. The combination of claim 5 wherein said elements are secured to said frame for resilient movement toward and away from the respective upper and lower sections to clamp said cotton rolls between said elements and said front portions.

7. An appliance according to claim 1 including a tongue depressor carried by said frame and extending generally along and within the confines of said lower section.

8. An appliance according to claim 1 wherein said frame is formed of metallic wire.

9. An appliance according to claim 1 including tabs extending forwardly from each of said upper and lower front portions for pivoting said sections toward one another upon insertion and withdrawal of the appliance relative to the patient's mouth.

10. A dental appliance for isolating an operating area of the mouth of a human patient and maintaining the mouth in an open position comprising:
   a frame including upper and lower generally U-shaped sections in spaced relation one to the other and generally conformal in shape to the spaces between the upper gum and lip and lower gum and lip, respectively, of the mouth of a human patient, each section having a front portion and a pair of transversely spaced leg portions extending rearwardly from the front portion;
   the leg portions of said sections being connected to ne another adjacent rear end portions thereof and transverse opposite sides of the appliance;
   said connected rear and leg portions forming a resilient connection between said upper and lower sections, enabling movement of said upper and lower sections toward and away from one another about an axis extending generally transversely of said appliance;
   said resilient connection maintaining said upper and lower sections spaced in an operative orientation a predetermined distance one from the other such that, upon placement of the appliance in a patient's mouth, the appliance maintains the patient's mouth in an open position; and
   means carried by said frame for securing a flexible material along the front portions of each of the upper and lower sections thereof enabling the material to cushion the appliance frame between the gums and lips of the patient;
   said securing means including a mesh material carried by said upper and lower frame sections.

11. A dental appliance for isolating an operating area of the mouth of a human patient and maintaining the mouth in an open position comprising:
   a frame including upper and lower generally U-shaped sections in spaced relation one to the other and generally conformal in shape to the spaces between the upper gum and lip and lower gum and lip, respectively, of the mouth of a human patient, each section having a front portion and a pair of transversely spaced leg portions extending rearwardly from the front portion;
   the leg portions of said sections being connected to one another adjacent rear end portions thereof and transverse opposite sides of the appliance;
   said connected rear and leg portions forming a resilient connection between said upper and lower sections, enabling movement of said upper and lower sections toward and away from one another about an axis extending generally transversely of said appliance;
   said resilient connection maintaining said upper and lower sections spaced in an operative orientation a predetermined distance one from the other such that, upon placement of the appliance in a patient's mouth, the appliance maintains the patient's mouth in an open position; and
   means carried by said frame for securing a flexible material along the front portions of each of the upper and lower sections thereof enabling the material to cushion the appliance frame between the gums and lips of the patient;
   said securing means including a pair of elements connected to said frame and extending along and in spaced, generally parallel relation to said upper and lower sections for securing at least part of the flexible material between said elements and said upper and lower section, respectively, said elements lying between said front portions of said upper and lower sections.

12. A dental appliance for isolating an operating area of the mouth of a human patient and maintaining the mouth in an open position comprising:
   a frame including upper and lower generally U-shaped section in spaced relation one to the other and generally conformal in shape to the spaces between the upper gum and lip and lower gum and lip, respectively, of the mouth of a human patient, each section having a front portion and a pair of transversely spaced leg portions extending rearwardly from the front portion;
   the leg portions of said sections being connected t one another adjacent rear end portions thereof and transverse opposite sides of the appliance;
   said connected rear and leg portions forming a resilient connection between said upper and lower sections, enabling movement of said upper and lower sections toward and away from one another about an axis extending generally transversely of said appliance;
   said resilient connection maintaining said upper and lower sections spaced in an operative orientation a predetermined distance one from the other such that, upon placement of the appliance in a patient's mouth, the appliance maintains the patient's mouth in an open position;
   a flexible material; and
   means carried by said frame for securing said flexible material along the front portions of each of the upper and lower sections thereof enabling the material to cushion the appliance frame between the gums and lips of the patient;
   said securing means including a mesh material carried by said upper and lower frame sections.

13. The combination of claim 12, wherein said flexible material comprises a wrapping of said material about each of said upper and lower sections including said mesh material.

14. The combination according to claim 12, wherein said flexible material comprises an absorbent cotton roll.

* * * * *